(12) United States Patent
Bellamy

(10) Patent No.: US 9,173,833 B2
(45) Date of Patent: Nov. 3, 2015

(54) ANHYDROUS ANTIPERSPIRANT COMPOSITIONS

(71) Applicant: Conopco, Inc., Englewood Cliffs, NJ (US)

(72) Inventor: Graham Lee Bellamy, Leeds (GB)

(73) Assignee: Conopco, Inc., Englewood Cliffs, NJ (US)

( * ) Notice: Subject to any disclaimer, the term of this patent is extended or adjusted under 35 U.S.C. 154(b) by 41 days.

(21) Appl. No.: 14/362,606

(22) PCT Filed: Nov. 14, 2012

(86) PCT No.: PCT/EP2012/072627
§ 371 (c)(1),
(2) Date: Jun. 4, 2014

(87) PCT Pub. No.: WO2013/087333
PCT Pub. Date: Jun. 20, 2013

(65) Prior Publication Data
US 2015/0037264 A1    Feb. 5, 2015

(30) Foreign Application Priority Data
Dec. 12, 2011 (EP) .................................... 11192968

(51) Int. Cl.
| | | |
|---|---|---|
| *A61K 8/96* | (2006.01) | |
| *A61K 8/39* | (2006.01) | |
| *A61K 8/04* | (2006.01) | |
| *A61K 8/19* | (2006.01) | |
| *A61K 8/26* | (2006.01) | |
| *A61Q 15/00* | (2006.01) | |
| *A61K 8/28* | (2006.01) | |
| *A61K 8/20* | (2006.01) | |
| *A61K 8/86* | (2006.01) | |

(52) U.S. Cl.
CPC ................ *A61K 8/965* (2013.01); *A61K 8/044* (2013.01); *A61K 8/19* (2013.01); *A61K 8/20* (2013.01); *A61K 8/26* (2013.01); *A61K 8/28* (2013.01); *A61K 8/39* (2013.01); *A61K 8/86* (2013.01); *A61Q 15/00* (2013.01); *A61K 2800/58* (2013.01)

(58) Field of Classification Search
None
See application file for complete search history.

(56) References Cited

U.S. PATENT DOCUMENTS

| | | |
|---|---|---|
| 3,792,068 A | 2/1974 | Luedders |
| 3,963,833 A | 6/1976 | DeSalva |
| 5,955,065 A * | 9/1999 | Thong ...................... A61K 8/19 424/400 |
| 6,045,784 A | 4/2000 | Ruebusch |
| 6,248,312 B1 | 6/2001 | Franklin |
| 6,294,180 B1 | 9/2001 | Demars |
| 6,410,001 B1 | 6/2002 | Franklin |
| 6,410,003 B1 | 6/2002 | Bhatia |
| 6,902,723 B2 | 6/2005 | Shen |
| 7,332,153 B2 | 2/2008 | Bhatia |
| 2003/0211062 A1* | 11/2003 | Laden .................... A61K 8/042 424/70.1 |
| 2012/0177589 A1 | 7/2012 | Banowski |

FOREIGN PATENT DOCUMENTS

| | | |
|---|---|---|
| DE | AT414096 B | 9/2006 |
| EP | 0545556 A2 | 6/1993 |
| EP | 1000608 A1 | 5/2000 |
| WO | WO9827954 A1 | 7/1998 |
| WO | WO2010078917 A2 | 7/2010 |
| WO | WO2010105030 A1 | 9/2010 |

OTHER PUBLICATIONS

Proksch et al., "Bathing in a magnesium-rich Dead Sea salt solution improves skin barrier function, enhances skin hydration, and reduces inflammation in atopic dry skin", International Journal of Dermatology, 2005, vol. 44, pp. 151-157.
Soroka et al., "Aged keratinocyte phenotyping: Morphology, biolchemical markers and effects of Dea Sea minerals", Experimental Gerontology, Aug. 2008, vol. 43, pp. 947-957.
"1987—The Year of Enhanced Efficacy Antiperspirants", The Reheis Report of 1987, vol. V, pp. 1-6.
PCT International Search Report in PCT application PCT/EP2012/072627 dated Mar. 1, 2013 with Written Opinion.
European Search Report in EP application EP 11 19 2968 dated Aug. 24, 2012 with Written Opinion.

* cited by examiner

*Primary Examiner* — Mina Haghighatian
*Assistant Examiner* — Erin Hirt
(74) *Attorney, Agent, or Firm* — Karen E. Klumas

(57) ABSTRACT

An antiperspirant composition comprising a suspension of from 1 to 50% of an aluminium and/or zirconium containing antiperspirant active, a carrier substance in which the antiperspirant active is insoluble, and a poly(ethylene glycol) solution of a polyelectrolyte salt comprising sodium, potassium, magnesium, calcium, chloride and bromide ions, the weight ratio of sodium to the other named cations being less than 3:2 and the weight ratio of the bromide to chloride anion being greater than 1:99, in said solution.

14 Claims, No Drawings

ANHYDROUS ANTIPERSPIRANT COMPOSITIONS

The present invention is in the field of cosmetic compositions, in particular anhydrous antiperspirant compositions and their use in reducing perspiration.

A variety of antiperspirant compositions have been marketed for many years. They serve to reduce perspiration, particularly following application to the surface of the body. Such compositions are typically considered cosmetic products, although certain countries do classify the active ingredients most commonly used in such compositions as pharmaceutical agents. The compositions are most commonly applied to the underarm regions of the human body.

Many antiperspirant compositions are anhydrous in nature. The lack of water in such compositions is not only consistent with the consumer's desire to keep his or her body dry, but it can be essential for the effectiveness of certain common components and it can have desirably sensory benefits. In addition, there can be anti-corrosion benefits relating to the packaging, especially when the composition comprises free chloride ions.

Anhydrous antiperspirant stick compositions and aerosol compositions can contain "activated" antiperspirant actives of very high efficacy. Various publications in the trade literature describe such formulations. An example of such is The Reheis Report of 1987, Vol. V, "1987—The Year of Enhanced Efficacy Antiperspirants", p 1-6. This publication discloses anhydrous antiperspirant stick compositions comprising activated aluminium tetrachlorohydrex-Gly salts and anhydrous antiperspirant aerosol compositions comprising activated aluminium chlorohydrate salts.

Manufacturers of antiperspirant compositions have previously attempted to incorporate additional salts in said products.

U.S. Pat. No. 5,955,065 (Gillette) discloses the use of calcium salts to enhance the efficacy of certain antiperspirant actives.

U.S. Pat. No. 6,902,723 (Gillette) discloses the use of strontium salts to enhance the efficacy of certain antiperspirant actives.

Manufacturers of cosmetic and pharmaceutical compositions have previously attempted to formulate Dead Sea salt into their products.

AT 414,096 B (Franz and Erika) discloses topical formulations for treating nail and foot fungus comprising Dead Sea salt, amongst other components.

EP 1,000.608 (L'Oreal) discloses skin care powders comprising Dead Sea salt.

Consumers are increasingly desirous of applying "natural" ingredients and treatments to their bodies. A traditional ingredient of this type is sea salt and especially Dead Sea salt, originating from the Dead Sea bordered by Jordan, West Bank and Israel. Salt from this source is considered particularly health promoting and many tourists visit the area each year to bathe in the water there.

There is scientific support for the health promoting benefits of Dead Sea salts. Regular use can improve the skin barrier function, enhance hydration and reduce inflammation (Proksch et al, Int. J. Dermatol., 2005, 44, 151-157). In addition, there can be stimulation of cellular proliferation and activity (Soroka et al, Exp. Gerontology, 2008, 43, 947-957).

It is an object of the present invention to provide a cosmetic composition that provides an antiperspirancy benefit and delivers Dead Sea salt or a similar electrolyte mixture to the surface of the human body.

It is a further object of the present invention to provide an anhydrous antiperspirant composition comprising Dead Sea salt or a similar electrolyte mixture.

Throughout this description, references to Dead Sea salt should to be understood to be to salts having an electrolyte mixture similar to Dead Sea salt, where possibly appropriate.

It is believed that by delivering both antiperspirancy and the real and/or perceived benefits of Dead Sea salt, the consumer will gain both physical and potentially emotional enhancements.

Incorporation of salts and particularly Dead Sea salt into anhydrous antiperspirant compositions is problematic. It is with the solution of these problems that the present invention is concerned.

The present inventor found that incorporating solid Dead Sea salt into anhydrous antiperspirant compositions was particularly problematic. In stick compositions, a gritty texture resulted, whilst in aerosol compositions valve blockage was an issue. Attempts to overcome these problems by reducing the particle size of the Dead Sea salt failed because of the highly hygroscopic and deliquescent nature of the salt, rendering it impossible to mill in a normal atmosphere.

The present inventor therefore looked into the possibility of dissolving the Dead Sea salt into the composition; however, this also proved problematic. Salts having the electrolyte balance (vide infra) of Dead Sea salt proved to be extremely difficult to dissolve. Indeed, Dead Sea salt proved to be insoluble in all of the commonly used liquid components of anhydrous antiperspirant compositions.

More polar solvents that might dissolve Dead Sea salt and yet still be compatible with an anhydrous antiperspirant composition were sought. The compatibility with the rest of the composition was particularly difficult because of the presence of the aluminium and/or zirconium containing antiperspirant active in the composition and the desire not to dissolve this component. Partial dissolution of this component can lead to numerous difficulties both in terms of the sensory properties of the product and the delivery and effectiveness of the active. A particular problem with partial dissolution of the antiperspirant active is that the composition can become gritty, undesirably both for sensory reasons and visual appearance. A further problem that can arise with aerosol products is poor dispensing when there is partial dissolution of the antiperspirant active, due to the nozzle becoming blocked.

In a first aspect of the present invention, there is provided an anhydrous antiperspirant composition comprising a suspension of from 1 to 50% of an aluminium and/or zirconium containing antiperspirant active, a carrier substance in which the antiperspirant active is insoluble, and a poly(ethylene glycol) solution of a polyelectrolyte salt comprising sodium, potassium, magnesium, calcium, chloride and bromide ions, the weight ratio of sodium to the other named cations being less than 3:2, in said solution.

In a second aspect of the present invention, there is provided a method of reducing perspiration comprising the topical application of a composition according to the first aspect of the invention.

In a third aspect of the present invention, there is provided a method of manufacture of an anhydrous antiperspirant composition comprising the dissolution in poly(ethylene glycol) of a polyelectrolyte salt comprising sodium, potassium, magnesium, calcium, chloride and bromide ions, the ratio of sodium to the other named cations in said salt being less than 3:2, the mixing of the so formed poly(ethylene glycol) solution of polyelectrolyte salt into a carrier substance and, before or after said mixing, the introduction of from 1 to 50% of an aluminium and/or zirconium containing antiperspirant active into the carrier substance, the antiperspirant active being insoluble in the carrier substance.

The method for reducing perspiration described herein is for reducing perspiration from the surface of the human body, in particular from the underarm areas and the feet and especially from the underarm areas, otherwise known as the axillae.

The method may generally be considered a cosmetic method and compositions used in achieving the method, cosmetic compositions.

Herein, references to "stick" compositions should be understood to be compositions suitably for application from stick-type dispensers, including soft solid and gel compositions.

Herein, percentages should be understood to be percentages by weight, unless otherwise indicated.

Herein, the term "anhydrous" should be understood to mean having less than 2% by weight of free water; "free water" being water other than the water of hydration associated with any particular component. Preferably, anhydrous compositions have less than 1% by weight free water and more preferably less than 0.5%.

It is preferred that anhydrous compositions have a total water content (including water of hydration associated with components therein) of less than 10% by weight, and more preferably less than 5%.

Herein, the terms "liquid" and "solid" should be understood to refer to states of matter observed at 20° C. and 1 atmosphere pressure.

Herein, the term "insoluble" should be understood to refer to a material having a solubility of less than 0.1 g/100 g at 20° C. in potential solvent indicated.

Antiperspirant actives for use in compositions of the invention contain aluminium and/or zirconium. They are typically astringent salts. Preferred salts are halohydrate salts, such as chlorohydrates.

The total amount of antiperspirant actives incorporated in compositions of the invention is from 1 to 50%, and preferably from 2 to 40%. In stick compositions, it is preferably from 10 to 40% and more preferably from 15 to 35%. In aerosol compositions, it is preferably from particularly from 1 to 30% and more preferably from 2% to 10%.

Particularly suitable aluminium-containing actives are halohydrates defined by the general formula $Al_2(OH)_xQ_y.wH_2O$ in which Q represents chlorine, bromine or iodine, x is variable from 2 to 5 and x+y=6 while $wH_2O$ represents a variable amount of hydration. Especially effective aluminium halohydrate salts are known as activated aluminium chlorohydrates and are made by methods known in the art.

Particularly suitable zirconium-containing actives are represented by the empirical general formula: $ZrO(OH)_{2n-nz}B_z.wH_2O$ in which z is a variable in the range of from 0.9 to 2.0 so that the value 2n-nz is zero or positive, n is the valency of B, and B is selected from the group consisting of chloride, other halide, sulphamate, sulphate and mixtures thereof.

Particularly in stick compositions, it is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine.

Preferred antiperspirant actives are activated, that is to say, of enhanced efficacy. Such activated salts are typically prepared by procedures that reduce the water content of said salts.

Particularly preferred antiperspirant actives are activated aluminium chlorohydrates, especially for use in aerosol compositions and activated aluminium-zirconium chlorohydrate glycine complexes, especially for use in stick compositions.

The amount of solid antiperspirant salt in a suspension composition includes the weight of any water of hydration and any complexing agent that may also be present in the solid active.

The particle size of the antiperspirant salts often falls within the range of 0.1 to 200 μm and particularly from 0.2 to 100 μm, some desirable products having at least 95% by weight of below 50 μm with a mean particle size often from 3 to 30 μm and in many instances from 5 to 20 μm.

The carrier substance for the antiperspirant active is one in which said antiperspirant active is insoluble. The carrier substance is also one that is cosmetically acceptable. More than one carrier substance may be employed.

The total amount of carrier substances is preferably from 20% to 90% and or more preferably from 30% to 85% of the weight of the composition, excluding any volatile propellant that may be present.

Preferred compositions of the invention comprise a liquid carrier substance, although this may be incorporated into a stick composition that is solid in nature.

Preferably, such carrier substances are anhydrous, as described hereinabove. Preferably, carrier materials contain less than 2%, more preferably less than 1% and most preferably less than 0.5% by weight free water.

Preferred liquid carrier substances also perform an additional function; particularly preferred liquid carrier materials are emollients and/or masking oils.

Preferred carrier materials are hydrophobic. Hydrophobic liquid carrier substances particularly suitable for use are liquid silicones, that is to say, liquid polyorganosiloxanes. Such materials may be cyclic or linear, examples include Dow Corning silicone fluids 344, 345, 244, 245, 246, 556, and the 200 series; Union Carbide Corporation Silicones 7207 and 7158; and General Electric silicone SF1202. Alternatively, non-silicone hydrophobic liquids may be used. Such materials include mineral oils, hydrogenated polyisobutene, polydecene, paraffins, isoparaffins of at least 10 carbon atoms, ether oils such as PPG-14 butyl ether, and aliphatic or aromatic ester oils (e.g. triethyl hexanoin, isopropyl myristate, lauryl myristate, isopropyl palmitate, diisopropyl sebecate, diisopropyl adipate, or $C_8$ to $C_{18}$ alkyl benzoates). Particularly preferred carrier materials are ester oils, in particular C12-15 alkyl benzoate, available as Finsolv TN from Finetex. In certain preferred embodiments, sunflower seed oil may be included, optionally with a branched chain fatty alcohol, such octyl dodecanol.

A poly(ethylene glycol) solution of a polyelectrolyte salt as described in the first aspect of the invention is an essential feature of the present invention.

Herein, the abbreviation PEG is used to represent poly (ethylene glycol). When this abbreviation is followed by a number, e.g. PEG4, the number represents how many PEG repeat units are in the material. Hence, PEG4 has the following structure:

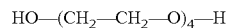

The PEG may be of any molecular weight, although is preferred that the PEG is a liquid at 20° C., having an average molecular weight of from 100 to 900.

Herein average molecular weights are number average molecular weights.

For the avoidance of doubt, the term poly(ethylene glycol) includes di(ethylene glycol) or PEG2; however, the most preferred PEG is PEG4.

The polyelectrolyte salt dissolved in the PEG comprises sodium, potassium, magnesium, calcium, chloride and bromide ions, in such amounts that the weight ratio of sodium to the other named cations is less than 3:2.

The weight ratio of sodium to the other named cations in the PEG solution is preferably less than 1:1 and more preferably from 1:4 to 2:3.

The weight ratio of magnesium to the other named cations in the PEG solution is preferably 1:3 or greater and more preferably from 1:2 to 1:1.

The weight ratio of calcium to the other named cations in the PEG solution is preferably 1:100 or greater and more preferably from 1:100 to 1:5.

The weight ratio of potassium to the other named cations in the PEG solution is preferably 1:20 or greater and more preferably from 1:5 to 3:2. In certain preferred embodiments, the potassium may as high as from 2:3 to 3:2.

The most preferred polyelectrolyte levels are similar to those found in Dead Sea salt, having the following relative amounts by weight of cations: from 25 to 45% magnesium; from 10 to 50% sodium; from 1 to 20% calcium; and from 5 to 55% potassium. By contrast, normal ocean sea water has the following relative amounts by weight of cations: 10% magnesium; 84% sodium; 3% calcium, and 3% potassium. We found Dead Sea salt much harder to formulate than normal ocean sea water because of the higher levels of more hygroscopic and deliquescent materials in the former.

The weight ratio of bromide anions to chloride anions in the PEG solution is preferably 1:200 or greater and more preferably 1:100 or greater, as is generally found in Dead Sea salt. By contrast, normal ocean sea water comprise bromide ion as 0.3% by weight of the total anions present, the vast majority of the remaining anion content being chloride.

A suitable polyelectrolyte salt sold as Dead Sea salt (Maris Sal) by A. & E. Connock has following composition: from 30 to 35% magnesium chloride, from 22 to 28% potassium chloride; from 4 to 18% sodium chloride; from 0.3 to 0.7% calcium chloride; from 0.2 to 0.6% bromide ion; and from 0.05 to 0.20% sulphate ion. This balance of this raw material comprises water and minor levels (0.05 to 0.9%) of insoluble matter.

The polyelectrolyte salt as described herein is typically dissolved the PEG at a level of from 0.1 to 15%, more typically at from 1 to 10%, and most commonly at from 5 to 10% by weight of the solution.

The PEG solution of the polyelectrolyte salt is preferably incorporated into compositions at a level of from 0.005 to 10%.

The total level of PEG in compositions of the invention, whether added with dissolved polyelectrolyte salt or not, is preferably from 0.005% to 20% and more preferably from 0.005 to 5%.

The total level of dissolved polyelectrolyte salt as described herein, in compositions of the invention, is preferably from 5 ppm to 1% and more preferably from 10 ppm to 0.1% by weight.

The PEG solution of the polyelectrolyte salt is preferably uniformly dispersed throughout the composition, giving a homogeneous mixture. This may be as a true solution or there may be discrete droplets of the PEG solution dispersed uniformly through the composition as a whole.

In certain embodiments in may be desirable to include an additional deodorant active. When employed, the level of incorporation is preferably from 0.01% to 3% and more preferably from 0.03% to 0.5% by weight. Preferred deodorant actives are those that are more efficacious than simple alcohols such as ethanol. Examples include quaternary ammonium compounds, like cetyltrimethylammonium salts; chlorhexidine and salts thereof; and diglycerol monocaprate, diglycerol monolaurate, glycerol monolaurate, and similar materials, as described in "Deodorant Ingredients", S. A. Makin and M. R. Lowry, in "Antiperspirants and Deodorants", Ed. K. Laden (1999, Marcel Dekker, New York). More preferred are polyhexamethylene biguanide salts (also known as polyaminopropyl biguanide salts), an example being Cosmocil CQ available from Arch Chemicals; 2',4,4'-trichloro,2-hydroxy-diphenyl ether (triclosan); and 3,7,11-trimethyl-dodeca-2,6,10-trienol (farnesol).

Other components particular to the type of composition in which the invention is used may also be included. Types of composition in which the invention may be used include, non-exclusively, sticks, including soft solids; aerosols; and roll-ons.

Stick compositions typically comprise one or more structurants or gellants, which serve to thicken the composition. Such thickeners, referred to as structurant systems, may be selected from those known in the art for such purpose. It has been found that particularly suitable structurant systems comprise:

1. stearyl alcohol as the major component, preferably in the presence of lesser amounts of polyethylene wax and hydrogenated castor oil; or
2. polyethylene wax as the major component, preferably in the presence of lesser amount of hydrogenated castor oil.

In general, structurant and gellants suitable for use in compositions according to the present invention may be classed as waxes or non-polymeric fibre-forming gellants.

"Waxes" may be defined as water-insoluble materials that are solid at 30° C. and preferably also at 40° C. They may be selected from hydrocarbons, linear fatty alcohols, silicone polymers, esters waxes or mixtures thereof.

Examples of hydrocarbon waxes include paraffin wax, ozakerite, microcrystalline wax and polyethylene wax, the last named desirably having an average molecular weight of from 300 to 600 and advantageously from 350 to 525.

Linear fatty alcohols commonly contain from 14 to 40 carbon atoms and often from 16 to 24. In practice, most contain an even number of carbon atoms and many comprise a mixture of compounds, even those that are nominally a single one such as stearyl alcohol.

Silicone polymer waxes typically satisfy the empirical formula:—

$$R\text{—}(SiMe_2\text{-}O\text{—})_x\text{—}SiMe_2R \qquad 1.$$

in which x is at least 10, preferably 10 to 50 and R represents an alkyl group containing at least 20 carbons, preferably 25 to 40 carbons, and particularly having an average linear chain length of at least 30 carbons; or

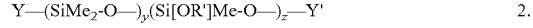

$$Y\text{—}(SiMe_2\text{-}O\text{—})_y(Si[OR']Me\text{-}O\text{—})_z\text{—}Y' \qquad 2.$$

in which Y represents $SiMe_2$-O, Y' $SiMe_2$, R' an alkyl of at least 15 carbons preferably 18 to 22 such as stearyl, y and z are both integers, totalling preferably from 10 to 50.

Examples of ester waxes include esters of $C_{16}$-$C_{22}$ fatty acids with glycerol or ethylene glycol, which can be isolated from natural products or more conveniently synthesised from the respective aliphatic alcohol and carboxylic acid.

"Non-polymeric fibre-forming gellants" are capable of being dissolved in a water-immiscible blend of oils at elevated temperature and on cooling precipitating out to form a network of very thin strands that are typically no more than a few molecules wide. One particularly effective category of such thickeners comprises N-acyl aminoacid amides and in particular linear and branched N-acyl glutamic acid dialkylamides, such as in particular N-lauroyl glutamic acid di n-butylamide and N-ethylhexanoyl glutamic acid di n-butylamide and especially mixtures thereof. Such amido gellants can be employed in anhydrous compositions according to the present invention, if desired, with 12-hydroxystearic acid.

Other such non-polymeric fibre-forming gellants include 12-hydroxystearic acid amides, and amide derivatives of di- and tri-basic carboxylic acids as set forth in WO 98/27954, including notably alkyl N,N'dialkyl succinamides.

Further suitable structuring systems comprising non-polymeric fibre-forming gellants of this type are described in U.S. Pat. Nos. 6,410,003, 7,332,153, 6,410,001, 6,321,841, 6,248,312.

The structurant or gellant is often employed in the stick or soft solid composition at a concentration of from 1.5 to 30%. When a non-polymeric fibre-forming gellants is employed as the major component of the structuring system, its concentration is typically in the range of from 1.5 to 7.5% by weight for amido gellants or mixtures of them and for 5 to 15% for ester or sterol gellants. When a wax is employed as the major component of the structuring system, its concentration is usually selected in the range of from 10 to 30% by weight, and particularly from 12 to 24% by weight.

Other types of structurant or gellant disclosed in the prior art may alternatively be employed.

Aerosol compositions suitable for use in accordance with the invention are characterised by comprising a propellant, typically a liquefied hydrocarbon or halogenated hydrocarbon gases (particularly fluorinated hydrocarbons such as 1,1-difluoroethane and/or 1-trifluoro-2-fluoroethane) that have a boiling point of below 10° C. and especially those with a boiling point below 0° C. It is especially preferred to employ liquified hydrocarbon gases, and especially $C_3$ to $C_6$ hydrocarbons, including propane, butane, isobutane, pentane and isopentane and mixtures of two or more thereof. Preferred propellants are isobutane, isobutane/propane, butane/propane and mixtures of propane, isobutane and butane.

Other propellants that can be contemplated include alkyl ethers, such as dimethyl ether or compressed non-reactive gasses such air, nitrogen or carbon dioxide.

The propellant is typically the major component of aerosol compositions, often comprising from 30 to 99% weight and preferably comprising from 50 to 95% by weight.

In certain preferred embodiments, aerosol compositions may also comprise a liquid carrier substance other than the propellant. These may be selected as appropriate from those previously mentioned, hydrophobic liquid carrier materials being especially preferred.

In certain preferred embodiments, aerosol compositions may also comprise a suspending agent, for example, a hydrophobically modified clay, such as disteardimonium hectorite (Bentone 38V), ex Elementis, typically at from 0.1 to 1.5% by weight.

Propylene carbonate may also be advantageously employed in aerosol compositions used in accordance with the present invention, typically at from 0.001 to 0.1% by weight.

Roll-on compositions suitable for use in accordance with the invention are suspensions of antiperspirant active in an anhydrous liquid carrier substance (vide supra), hydrophobic liquid carrier substances being preferred.

Roll-on compositions preferably comprise a suspending agent, for example, a hydrophobically modified clay, such as disteardimonium hectorite (Bentone 38V), ex Elementis, typically at from 0.5 to 3% by weight.

Roll-on compositions preferably comprise a particulate sensory modifier, for example finely divided clay such as Aerosil 200, ex Evonik Degussa, typically at from 0.01 to 0.5% by weight.

Certain sensory modifiers are further desirable components in the compositions of the invention. Such materials are preferably used at a level of up to 20% by weight of the composition. Emollients, humectants, volatile oils, non-volatile oils, and particulate solids that impart lubrication are all suitable classes of sensory modifiers. Examples of such materials include cyclomethicone, dimethicone, dimethiconol, isopropyl myristate, isopropyl palmitate, talc, finely-divided silica (e.g. Aerosil 200), particulate polyethylene (e.g. Acumist B18), polysaccharides, corn starch, C12-C15 alcohol benzoate, PPG-3 myristyl ether, octyl dodecanol, C7-C14 isoparaffins, di-isopropyl adipate, isosorbide laurate, PPG-14 butyl ether, glycerol, hydrogenated polyisobutene, polydecene, titanium dioxide, phenyl trimethicone, dioctyl adipate, and hexamethyl disiloxane.

In certain compositions, emulsifiers that are perfume solubilisers and/or wash-off agents are preferred additional components. Examples of the former include PEG-hydrogenated castor oil, available from BASF in the Cremaphor RH and CO ranges, preferably present at up to 1.5% by weight, more preferably 0.3 to 0.7% by weight. Examples of the latter include poly(oxyethylene) ethers.

In many embodiments of the invention, fragrance is a desirable additional component. Suitable materials include conventional perfumes, such as perfume oils and also include so-called deo-perfumes, as described in EP 545,556, for example. Levels of incorporation are preferably up to 5% by weight, particularly from 0.1% to 3.5% by weight, and especially from 0.5% to 2.5% by weight. The fragrance may also be added in an encapsulated form, release being triggered post-application by hydrolysis or shear on the surface of the human body.

Further additional components that may also be included are colourants and preservatives at a conventional level, for example $C_1$-$C_3$ alkyl parabens or butylated hydroxytoluene, BHT.

The manufacture of compositions according to the invention involves a preliminary step of dissolving the polyelectrolyte salt in the PEG. This step typically involves shearing the salt into the PEG, typically for up to one hour. Optionally, this process may be conducted at elevated temperature, at 30, 40, or even 50° C., for example. Following this step, the PEG solution is incorporated into the composition and processing conditions suitable to the form of composition under manufacture are employed.

In preparing aerosol compositions, it is preferred that the Dead Sea salt solution is added together with a suspending agent, for example, a hydrophobically modified clay, such as disteardimonium hectorite (Bentone 38V), as described earlier. We have found that the suspending agent can act as a carrier for the Dead Sea salt solution and aid its incorporation into the composition.

In a preferred process of manufacture of an anhydrous aerosol base composition, the Dead Sea salt is added with the fragrance using shear to help it bind to a suspending agent that is present is in the nascent base together with an oil carrier substance. The antiperspirant active is then added with shear.

The anhydrous aerosol base composition should be understood to be an anhydrous aerosol composition without the propellant. Typically, liquefied volatile propellant is added to the former to give the latter.

EXAMPLES

The following examples illustrate certain specific embodiments of the invention and do not limit the scope of the invention. Examples according to the invention are indicated by numbers and comparative examples are indicated by letter. All amounts indicated are percentages by weight, unless otherwise indicated.

As preparatory step for the manufacture of the following Examples, a solution of Dead Sea salt in PEG4 may be prepared in the following manner.

80 g of Dead Sea salt (ex Cosmetochem International AG) is placed in a beaker with 720 g PEG4 (ex Clariant and having a water content of less than 0.5%). The mixture is stirred with a Silverson LM5 mixer, slowly increasing the shear rate to 5000 rpm and continuing stirring for 60 minutes. The mixture is then passed through a 125 micron sieve to remove any trace impurities.

Examples 1 to 3 indicated in Table 1 may be prepared in the following manner. The oils [components (1) to (3)] are blended together at 90° C. and the waxes [components (4) to (6)] are melted in with stirring. When the waxes are fully melted, the mixture is cooled to 75-80° C. and the antiperspirant active (7) and Dead Sea salt solution (8) (prepared as described above) are dispersed into the mixture. Finally, the fragrance and preservative are added and the mixture cooled to about 62° C. and poured into a stick barrel.

In a comparative example, it was attempted to formulate the the Dead Sea salt in a propylene glycol solution. This proved unsuccessful, the Dead Sea salt being insufficiently soluble in the propylene glycol.

In a further comparative example, it was attempted to formulate the Dead Sea salt in a di(propylene glycol) solution. This also proved unsuccessful, the Dead Sea salt being insufficiently soluble in the di(propylene glycol).

Examples 4 and 5 indicated in Table 1 may be prepared as follows. The oils [components (1) to (3)] are blended together at 50° C. and then heated to 90° C. The waxes [components (4) to (6)] are melted in with stirring. When the waxes are fully melted, the mixture is cooled to 75° C. and the antiperspirant active (7) is dispersed into the mixture. The mixture is further cooled to about 65° C. and Dead Sea salt solution (8) (prepared as described above), fragrance and preservative are added with stirring. In Example 5, the sunflower seed oil is then added with stirring. The final composition is then poured into stick barrels.

TABLE 1

Stick Compositions

| Component: | Example: | | | | |
|---|---|---|---|---|---|
| | 1 | 2 | 3 | 4 | 5 |
| Silicone oil (1) | To 100 | To 100 | To 100 | To 100 | To 100 |
| Ester oil (2) | 13.75 | 13.75 | 13.75 | 30 | 30 |
| Ether oil (3) | 8.00 | 8.00 | 8.00 | — | — |
| Stearyl alcohol (4) | 18.00 | 18.00 | 18.00 | — | — |
| Polyethylene wax (5) | 1.00 | 1.00 | 1.00 | 15 | 15 |
| Hydrogenated castor oil (6) | 3.50 | 3.50 | 3.50 | 2 | 2 |
| Sunflower seed oil | — | — | — | — | 0.5 |
| Reach 908 (7) | 24.00 | 24.00 | 24.00 | 24 | 24 |
| Dead Sea Salt in PEG4 (8) | 0.01 | 0.10 | 1.00 | 0.1 | 0.2 |
| Preservative | 0.05 | 0.05 | 0.05 | — | — |
| Fragrance | 1.00 | 1.00 | 1.00 | — | — |

(1) Cyclopentasiloxane, DC245, ex Dow Corning.
(2) C12-15 alkyl benzoate, Finsolv TN, ex Finetex.
(3) PPG-14 butyl ether, Fluid AP, ex Amerchol.
(4) Lanette C18 Deo, ex Cognis.
(5) Performalene 400, molecular weight ca. 400, ex Alfa Chemicals.
(6) Castor wax MP80, ex Caschem.
(7) Activated aluminium-zirconium tetrachlorohydrex-Gly, ex Summit Reheis.
(8) 10% solution of Dead sea salt (Maris Sal), ex A&E. Connock Ltd.
Further details of this raw material may be found in the description.

Antiperspirant aerosol Examples 6 to 9 indicated in Table 2 may be prepared as follows. The oils [component (1) and (2) or (3)] are blended at ambient temperature with the suspending agent [component (10)], propylene carbonate (when present), the Dead Sea salt solution (8) and the fragrance, added with shear. Finally, the AACH (9) is added, again with shear. The resulting base compositions are placed in aerosol cans which are closed with a standard valve and valve cup and the liquefied propellant [component (11)] then added.

TABLE 2

Aerosol Compositions

| Component: | Example: | | | | |
|---|---|---|---|---|---|
| | 6 | 7 | 8 | 9 | 10 |
| Silicone oil (1) | 2.89 | 2.875 | 2.875 | 2.875 | 2.10 |
| Ester oil (2) | — | — | 3.00 | 3.00 | 0.50 |
| Ether oil (3) | 3.00 | 3.00 | — | — | 2.89 |
| Sunflower seed oil | — | — | — | — | 0.52 |
| Octyl dodecanol (12) | — | — | — | — | 0.12 |
| Propylene carbonate | — | 0.015 | 0.015 | 0.015 | 0.015 |
| Fragrance | 1.00 | 1.00 | 1.00 | 1.00 | 1.00 |
| Dead Sea Salt in PEG4 (8) | 0.01 | 0.10 | 0.10 | 0.30 | 0.01 |
| AACH (9) | 5.00 | 5.00 | 2.00 | 4.00 | 5.00 |
| Suspending agent (10) | 0.5 | 0.5 | 0.5 | 0.5 | 0.55 |
| Propellant (11) | To 100 | To 100 | To 100 | To 100 | To 100 |

(1), (2), (3) and (8) as indicated under Table 1.
(9) AACH-7172, ex Summit.
(10) Disteardimonium hectorite, Bentone 38V, ex Elementis.
(11) CAP40, ex HARP.
(12) Eutanol G, ex Cognis.

The invention claimed is:

1. An anhydrous antiperspirant composition comprising a suspension of from 1 to 50% of an aluminium and/or zirconium containing antiperspirant active, a carrier substance in which the antiperspirant active is insoluble, and a poly(ethylene glycol) solution of a polyelectrolyte salt comprising sodium, potassium, magnesium, calcium, chloride and bromide ions, the weight ratio of sodium to the other named cations being less than 3:2, in said solution.

2. An anhydrous antiperspirant composition according to claim 1, wherein the poly(ethylene glycol) is liquid at 20° C., having an average molecular weight of from 100 to 900.

3. An anhydrous antiperspirant composition according to claim 2, wherein the poly(ethylene glycol) has precisely four repeat units.

4. An anhydrous antiperspirant composition according to claim 1, comprising an activated antiperspirant active.

5. An anhydrous antiperspirant composition according to claim 1, comprising a propellant gas and being in the form of an aerosol composition.

6. An anhydrous antiperspirant composition according to claim 5, comprising activated aluminium chlorohydrate.

7. An anhydrous antiperspirant composition according to claim 1, comprising a structuring agent and being in the form of a stick or soft solid.

8. An anhydrous antiperspirant composition according to claim 7, comprising an aluminium-zirconium tetrachlorohydrex-Gly salt.

9. An anhydrous antiperspirant composition according to claim 1, wherein the weight ratios in the poly(ethylene glycol) solution of magnesium to the other named cations is 1:2 or greater.

10. An anhydrous antiperspirant composition according to claim 1, wherein the weight ratios in the poly(ethylene glycol) solution of calcium to the other named cations in the solution is 1:10 or greater.

11. An anhydrous antiperspirant composition according to claim 1, wherein the weight ratios in the poly(ethylene glycol) solution of potassium to the other named cations in the solution is 1:20 or greater.

12. An anhydrous antiperspirant composition according to claim 1, wherein the poly(ethylene glycol) solution has the following relative amounts by weight of cations: from 35 to 45% magnesium; from 32 to 42% sodium; from 12 to 20% calcium; and from 5 to 9% potassium.

13. A method of reducing perspiration comprising the topical application of a composition according to claim 1.

14. A method of manufacture of an anhydrous antiperspirant composition comprising the dissolution in poly(ethylene glycol) of a polyelectrolyte salt comprising sodium, potassium, magnesium, calcium, chloride and bromide ions, the ratio of sodium to the other named cations in said salt being less than 3:2, the mixing of the so formed poly(ethylene glycol) solution of polyelectrolyte salt into a carrier substance and, before or after said mixing, the introduction of from 1 to 50% of an aluminium and/or zirconium containing antiperspirant active into the carrier substance, the antiperspirant active being insoluble in the carrier substance.

* * * * *